(12) United States Patent
Petrus

(10) Patent No.: US 6,399,093 B1
(45) Date of Patent: Jun. 4, 2002

(54) METHOD AND COMPOSITION TO TREAT MUSCULOSKELETAL DISORDERS

(75) Inventor: Edward J. Petrus, Austin, TX (US)

(73) Assignee: Advanced Medical Instruments, Austin, TX (US)

( * ) Notice: Subject to any disclaimer, the term of this patent is extended or adjusted under 35 U.S.C. 154(b) by 0 days.

(21) Appl. No.: 09/314,829

(22) Filed: May 19, 1999

(51) Int. Cl.[7] .............................................. A61L 15/16

(52) U.S. Cl. ....................... 424/448; 424/449; 424/450; 514/46; 514/507; 514/411; 514/568; 514/630

(58) Field of Search ................................ 514/629, 630, 514/568, 411, 46, 507; 424/448, 449, 450

(56) References Cited

U.S. PATENT DOCUMENTS

| | | | |
|---|---|---|---|
| 3,880,996 A | 4/1975 | Fisher | 424/184 |
| 3,895,107 A | 7/1975 | Morrison | 424/180 |
| 4,057,686 A | 11/1977 | Flecchi | 536/26 |
| 4,120,976 A | 10/1978 | Hosick | 424/282 |
| 4,190,673 A | 2/1980 | Eakins et al. | 424/324 |
| 4,296,130 A | 10/1981 | Herschler | 424/337 |
| 4,309,414 A | 1/1982 | Inagi et al. | 424/81 |
| 4,342,784 A | 8/1982 | Havemeyer et al. | 424/337 |
| 4,454,122 A | 6/1984 | Stramenthinoli et al. | 424/180 |
| 4,477,469 A | 10/1984 | Herschler | 424/522 |
| 4,500,511 A | 2/1985 | Kigasawa et al. | 424/81 |
| 4,533,675 A | 8/1985 | Brossi et al. | 514/480 |
| 4,543,251 A | 9/1985 | Kamishita | 424/81 |
| 4,663,345 A | 5/1987 | Mullane | 514/454 |
| 4,722,938 A | 2/1988 | Sunshine et al. | 514/479 |
| 4,748,174 A | 5/1988 | Veromesi | 514/226.5 |
| 4,764,603 A | 8/1988 | Zappia et al. | 536/26 |
| 4,775,667 A | 10/1988 | Saitoh et al. | 514/160 |
| 4,780,463 A | 10/1988 | Sunshine et al. | 514/226.5 |
| 4,863,748 A | 9/1989 | Herschler | 426/72 |
| 4,873,081 A | 10/1989 | Ogiso | 424/81 |
| 4,923,898 A | 5/1990 | Sunshine et al. | 514/557 |
| 4,933,184 A | 6/1990 | Tsuk | 424/449 |
| 4,948,588 A | 8/1990 | Kamiya et al. | 424/436 |
| 4,954,487 A | 9/1990 | Cooper et al. | 514/159 |
| 4,956,173 A | 9/1990 | Le Fur et al. | 424/63 |
| 4,973,605 A | 11/1990 | Herschler | 514/708 |
| 5,061,724 A | 10/1991 | Gertner | 514/420 |
| 5,071,878 A | 12/1991 | Herschler | 514/711 |
| 5,073,366 A | 12/1991 | Beck | 424/720 |
| 5,128,244 A | 7/1992 | Gennari | 435/113 |
| 5,166,328 A | 11/1992 | Kurobe et al. | 536/26 |
| 5,196,402 A | 3/1993 | Braganza et al. | 514/9 |
| 5,223,257 A | 6/1993 | Arora | 424/195.1 |
| 5,223,267 A | 6/1993 | Nichols | 424/489 |
| 5,229,130 A | 7/1993 | Sharma et al. | 424/449 |
| 5,238,933 A | 8/1993 | Catz et al. | 514/236.2 |
| 5,364,845 A | 11/1994 | Henderson | 514/54 |
| 5,374,661 A | 12/1994 | Betlach, II | 514/772.4 |
| 5,466,678 A | 11/1995 | Kawabata | 514/46 |
| 5,482,965 A | 1/1996 | Rajadyyasha | 514/452 |
| 5,604,206 A | 2/1997 | Paradies | 514/23 |
| 5,620,980 A | 4/1997 | Samour | 514/256 |
| 5,624,675 A | 4/1997 | Kelly | 424/405 |
| 5,626,838 A | 5/1997 | Cavanaugh, Jr. | 424/54 |
| 5,719,197 A * | 2/1998 | Kanios et al. | 514/772.6 |
| 5,747,060 A | 5/1998 | Sackler et al. | 424/426 |
| 5,786,342 A | 7/1998 | Carpenter et al. | 514/54 |
| 5,807,957 A | 9/1998 | Samour et al. | 528/49 |
| 5,811,558 A | 9/1998 | Adgell et al. | 548/427 |
| 5,814,659 A | 9/1998 | Elden | 514/452 |
| 5,824,659 A | 10/1998 | Strickland et al. | 514/54 |
| 5,837,289 A | 11/1998 | Grasela et al. | 424/484 |
| 5,843,468 A * | 12/1998 | Burkoth et al. | 424/448 |
| 5,843,910 A | 12/1998 | Bombardelli et al. | 514/33 |
| 5,880,160 A | 3/1999 | Bombardelli et al. | 514/628 |
| 6,267,984 B1 * | 7/2001 | Beste et al. | 424/449 |

OTHER PUBLICATIONS

Osborne DW, Henke JJ, Skin Penetration Enhancers Cited in the Technical Literature; *Pharmaceutical Technology*, Nov. 1997, pp. 58–86.

Ringer M, Which NSAID for Acute Joint Pain?, *Patient Care*, Feb. 28, 1998, pp. 17–41.

Field TS, J. Am. Geriatr. Soc., 1999; 47:507–511 (abstract).

Vaile JH, Davis P, Topical NSAIDs for Musuloskeleton Conditions, A Review of the Literature. *Drugs* (1998) Nov.; 56(5):783–99 (abstract).

APT L, Voo I, Isenberg JJ., A Randomized Clinichi Trial of the Nonstenuidale eye drop Diclufenac After Strabismus Surgery, Ophtalmology, Aug. 1998; 105(8):1445–52 (abstract).

Sandelmy J et al Local NSAID Gel (Eltenac) in the Treatment of Osteuarthrifis of the Knee. A Double Blind study Comparing Elternal with oral Declofehac & PlaceroGor, Scano J. Rheumatic 1997:26(4) 287–92 (abstract).

Bueno of , Leidenheimer Nj, Colchicine Immibits GABA(12) Recetrors indepenently of Microtubule Depolymenization, Neuropharmacology 1998; 37(3):383–90 (abstract).

Ben–Chetrit E, Levy M, does the lack of the P–Glycoprotein Efflux Pump Inneutrophils Explain the Efficacy of Colchicine in Fam Med Fever & Other Inflamation Disease, Med Hypothers Nov. 1998, 51(5):377–80 (abstract).

Sullivan TP, King Le Jr., Boyd AS. Colchicine In Dermatology J. Am. Acad. Dermatol. Dec. 1998,; 34(6):993–9 (abstract).

Murray M, Pizzonna J. Gout. Encyclopedia of Natural Medicine 2n Ed., Prima Publishing, Rocklin, CA 1998, pp. 489–496.

(List continued on next page.)

*Primary Examiner*—James H. Reamer

(57) ABSTRACT

A method and composition for the treatment of musculoskeletal disorders in mammals by the application of a topical composition comprising a permeation enhancing amount of one or more penetration enhancers, and one or more bio-affecting agents to provide anti-inflammatory relief and analgesia to the applied body part.

15 Claims, No Drawings

OTHER PUBLICATIONS

Doral MN et al., The Role of Irrigation with Colchicine and Diclophenac Sodiumin in Experimontal Gonarthrosis. First Biennial Cohoress of the International Society of Anthroscopy, Knee Surgery & Orthopence Sports Medicine, Buenos Aires, May 11–16, 1997 (abstract).

Pouliot M, et al., Monododium Urate Microerystals Induce Cyclo Oxygenase–2 In Human Moneytes *Blood* 1998 Warli; 91(5):1769–76.

Yamaguchi M, Role of Zinc In Bone Formation and Bone Resorption. *J. Optrace Elements and Experimental Medicine* 1998; 11:119–135.

Petrus FJ et al. Randomized, Double–Masred, Pacebo–Controlled Clinical Study of the Effectuenos of Zinc Acetate Lozenges on Common Cold Symptons in Allergy–Tested Subjects. *Current Therapeutic Research*, 1998; 59(9):595–607.

Pelletier JP et al., Reduced Prognossion of Experimental Osteoanthritis In Vivio by Selective Innibiton of Inducible Nitric Oxide Syntase. *Arithritis & Rhumatism* 1998; 41:1275–1286.

Clancy RM et al., The Role of Nitru Oxide in Iflammation and Immunity. *Arthritis & Rheumatism*, 1998; 41:1141–1151.

Cuajungco MP, Lees W, Zinc Metabolism in the Brain: Releuances to Heurodegonative Disorders. *Neurosol Dis.* 1997; 4(3–4);137–69 (abstract).

Dykman KD et al., The Effects of Nutritlomic Supplements on the Symptony of Fibromyalgia & Chronic Fatigue Syndrome Integr. Physiol. Behav. Sci. 1998, J Am–Man; 33(1):61–71 (abstract).

Rao P, et al., Colchine Down Regulators Lipopolysaccharine–Induced Granulocyte–Macnophage Colony–Stimulating Factor Production in Murine Macrophagus. J. Immunol. 1997, 159:3531–3539.

Kingery WS et al. Colcyicine Treatment of the Sciatic Nerve Neurogomic Extravasation, but does not affect Noeiceptive Tresholds on Collational Sprouting In Neuromatihic Or Nomvia. Ants. Pain, Jan. 1998; 74(1):11–20.

Chithra P, et al InFluence of Aloe Vera on the Glucosaminoglycany in the matrix of Healing Dermal D Wounds. J. Ethnopharmaocl, Jan. 1998, 59(3): 179–86 (abstract).

Chitmrad P et al. Influence of Aloe Vera on Collagen Turnover in Healing of Dermal Wounds in Rats. Indian J. Exp. Biol. Sep. 1998; 36(9): 896–901 (abstract).

Heggers JP et al; Effect of the Combination of Aloe Vera, Nitroglycerin, and L–Name on Wound Healing in the Rat Excisional Model, J.Altern Complement Med., 1997, Summer; 3(2):149–53 (abstract).

Barclay TS, Tsourouhis C, McCart Gm. Glucosamine, Ann. Pharmacother., May 1998; 32(5): 574–9 (abstract).

DaCamara CC, Dowles GV., Glucosamine Sulfate for Osteoarthritis., Ann. Pharmaicther May 1998; 32(5):580–7. (abstract).

* cited by examiner

METHOD AND COMPOSITION TO TREAT MUSCULOSKELETAL DISORDERS

FIELD OF THE INVENTION

A method and topical composition for the treatment of musculoskeletal disorders.

BACKGROUND OF THE INVENTION

The musculoskeletal system consists of bones, muscles and joints. Ten percent of medical visits to physicians are for disorders of the musculoskeletal system. Musculoskeletal disorder include: sprains, strains, tendinitis, tenosynovitis, fibromyalgia, osteoarthritis, rheumatoid arthritis, gout, pseudogout (calcium pyrophosphate deposition disease), polymyalgia rheumatica, bursitis, acute and chronic back pain and osteoporosis, which interfere with the normal performance of activities of daily living. Injuries include sprains, strains and tears of ligaments, tendons, muscles and cartilage damage. Pain is the most common symptom and is frequently caused by injury or inflammation. Besides pain, other symptoms such as stiffness, tenderness, weakness and swelling or deformity of affected parts are manifestations of musculoskeletal disorders. Sports injuries are a significant cause of musculoskeletal disorders resulting in pain, strain, sprains, stiffness and leg cramps.

Occupational injuries however, have become this country's most costly form of illnesses. The Bureau of Labor Statistics reported in 1992, that one half of the 2.3 million nonfatal occupational injuries and illnesses which resulted in days away from work involved musculoskeletal disorders. The Occupational Safety and Health Administration (OSHA) estimates in 1999, that more than 647,000 Americans suffer from injuries or illnesses due to work-related musculoskeletal disorders (WMSDs). These disorders account for more than 34% of all workdays lost to injuries and illnesses and cost employers $15 to $20 billion per year in direct workers' compensation costs and another $100 billion on lost productivity, employee turnover, and other indirect expenses. Cumulative trauma disorders (CTDs) frequently involve the upper extremities, such as wrists, shoulders or elbows. Carpal tunnel syndrome of the wrist has become the fastest growing occupational hazard in the United States today.

Arthritis, a musculoskeletal disorder, is the leading cause of disability in the United States. The Centers for Disease Control and Prevention (CDC) stated that arthritis and other rheumatic conditions accounted for about 744,000 hospitalizations and 4 million days of care in 1997. It is estimated that 43 million people are now affected and expected to increase to 60 million people by 2020. Arthritis costs the country about $65 billion a year.

Osteoporosis afflicts 200 million people worldwide and 25 million people in the U.S., of whom 80% are women, yet one man in three will also get osteoporosis. One woman in two over the age of 60 is likely to have an osteoporotic bone fracture. The incidence of hip fracture exceeds that of cancer of the breast, cervix and uterus combined. Sixteen percent of patients suffering hip fractures will die within six months, while 50% will require long-term nursing care. The estimated cost of treatment and care for osteoporosis and related fractures exceeds 10 billion per year in the U.S. alone.

Treatment usually consists of an oral ingestion of an analgesic such as nonsteroidal anti-inflammatory drugs (NSAIDs). Adverse side effects of oral NSAIDs, such as hypersensitivity, gastropathy, renal impairment, liver toxicity and prolonged bleeding merit concern in the very young and elderly. The use of topical analgesic compositions to treat musculoskeletal disorders is an effort to overcome the side effects of oral preparations with the advantage of delivering the analgesic directly to the affected body part.

SUMMARY OF THE INVENTION

This invention relates to a method for the treatment of musculoskeletal disorders in mammals by the application of a topical composition comprising a permeation enhancing amount of one or more penetration enhancers, and one or more bio-affecting agents to provide anti-inflammatory relief and analgesia to the applied body part.

DETAILED DESCRIPTION OF THE INVENTION

The components of the method and composition of the present invention will be discussed separately because no prior art embraces them as a solitary method or composition to reduce inflammation and provide analgesia to the affected body part due to musculoskeletal disorders. The topical composition of the present invention comprises one or more penetration enhancers and one or more bio-affective agents.

Penetration Enhancer

A penetration enhancer or permeation enhancer is an agent used to increase the permeability of the skin to a pharmacologically active agent to increase the rate at which the drug diffuses through the skin and enters the tissues and bloodstream. A chemical skin penetration enhancer increases skin permeability by reversibly altering the physiochemical nature of the stratum corneum to reduce its diffusional resistance. In a review of the technical and patent literature up to 1996, more than 275 different chemical compounds were found to be cited as skin penetration enhancers. Most of the compounds are generally recognized as safe (GRAS) ingredients that would often be considered inert by a formulator. Osborne D W, Henke J J, *Pharmaceutical Technology*, November. 1997, pp 58–86. The compounds cited in the article are incorporated by reference. Examples of penetration enhancers include: alcohols, such as ethanol and isopropanol, polyols, such as n-alkanols, limonene, terpenes, dioxolane, propylene glycol, ethylene glycol, other glycols, and glycerol; sulfoxides, such as dimethylsulfoxide (DMSO), dimethylformanide, methyl dodecyl sulfoxide, dimethylacetamide; esters, such as isopropyl myristate/palmitate, ethyl acetate, butyl acetate, methyl proprionate, capric/caprylic triglycerides, ketones; amides, such as acetamide oleates such as triolein; various surfactants, such as sodium lauryl sulfate; various alkanoic acids such as caprylic acid; lactam compounds, such as azone; alkanols, such as oleyl alcohol; dialkylamino acetates, and admixtures thereof.

A number of patents disclose the use of penetration enhancers to deliver medications transdermally. Grasela et al, U.S. Pat. No. 5,837,289, discloses the use of at least two separate penetration enhancers in a cream to deliver an extensive list of medications, Catz et al, U.S. Pat. No. 5,238,933, discloses a skin permeation enhancer composition comprising a lower aliphatic ester of a lower aliphatic carboxyl acid in combination with a lower alkanol to administer an active agent. Sharma et al, U.S. Pat. No. 5,229,130, discloses a vegetable oil-based skin permeation enhancer to deliver active agents through the skin. Tsuk, U.S. Pat. No. 4,933,184, discloses a transdermal composition that uses methanol either sequentially or simultaneously to deliver drugs. Havemeyer et al, U.S. Pat. No. 4,342,784, discloses a method of topically administering a gel with DMSO and carboxy polymethylene resin with a neutralizing agent to enable the skin salt to break down the gel to release the DMSO. Rajadhyaksha, U.S. Pat. No. 5,482,965, discloses a transdermal composition containing a dioxane. Samour, U.S. Pat. Nos. 5,620,980, 5,807,957, discloses the use of a dioxolane and urethane to treat hair loss. None of the above cited patents teach or suggest the use of the method or composition outlined in the present invention.

Bio-affecting Agents

The present invention relates to novel compositions for topical application and delivery of bio-affecting agents through the protective outer layer of the skin, into the underlying tissues and into the vascular network of the targeted body part. The term "bio-affecting agent" refers to any chemical substance or formulation which beneficially affects the body. The bio-affecting agents of the preferred composition comprises; analgesics, NSAIDs, anti-inflammatory agents, colchicine, S-adenosyl-methionine, methyl-sulfonyl-methane, antioxidants, anti-infectives, zinc compounds, amino sugars, aloe vera extracts, and other active agents to form a solution, suspension, cream, ointment, gel, film, or spray.

The concentration of the bio-affecting agents in the composition can also vary greatly and will be dependent upon may factors, e.g. type, bioavailability, potency, surface area to which it is applied, composition used and the amount of the penetrating agents used. The concentration of bio-affecting agents will vary from about 0.1 % to 25 % of the total composition, and may be suspended or dissolved.

A wide variety of therapeutic agents, known to provide beneficial effects when absorbed into the tissues and vascular network, in combination with a penetration enhancer, facilitates penetration through the skin and absorbed into the vascular network of the targeted body parts. This topical administration offers a significant advantage over oral administration of therapeutic agents by overcoming the difficulty of poor gastrointestinal absorption, by using a lower dosage than required orally, and allows more of the active agents to provide therapeutic relief Bio-affective agents to be used in the composition includes the following:

Analgesics

Pain is usually the presenting symptom of musculoskeletal disorders. The pain response is a protective reflex system warning an individual of tissue injury. Most commercial topical analgesics use a counter-irritant, such as methyl salicylate, menthol, camphor, eucalyptol and derivatives or mixtures thereof, or rubefacients, such as capsicum, oleoresin chloroform and the like, formulated as an ointment or gel.

The use of counter-irritants and rubefacients to achieve analgesia are well known in the art. Arora, U.S. Pat. No. 5,223,257, discloses an analgesic composition of methyl salicylate, olive oil, eucalyptus oil and isopropyl alcohol. Nichols, U.S. Pat. No. 5,223,267, discloses an analgesic composition of cellulosic powder, counter-irritant (salicylates, menthol, camphor, eucalyptol), analgesic (aspirin, triethanolamine salicylate, ibuprofen), steroid (hydrocortisone), mineral oil, emollient and alcohol. Fisher, U.S. Pat. No. 3,880,996, discloses a preparation of salicylate, menthol, polysiloxane and a vasodilator, such as histamine. Beck, U.S. Pat. No. 5,073,366, discloses a composition containing camphor and eucalyptus oil. Elden, U.S. Pat. No. 5,814,659, discloses a topical composition of a lidocaine analgesic, benzyl alcohol, urea, fatty acid, emulsifier, gel, preservative and organic base. Saitoh et al, U.S. Pat. No. 4,775,667, discloses a topical composition of ethylene glycol monosalicilate, methanol and a small amount of corticosteroid. Hosick, U.S. Pat. No. 4,120,976, discloses the use of methylenedioxyamphetamine to treat arthritis. None of the above cited patents teach or suggest the use of the method and composition outlined in the present invention.

Nonsteroidal Anti-inflammatory Agents

Nonsteroidal anti-inflammatory agents (NSAIDs) are also useful in relieving pain and tissue swelling, chiefly by inhibiting the biosynthesis of prostaglandins. In small doses, NSAIDs have an analgesic action, but full doses have both analgesic and anti-inflammatory actions, and are effective in reducing pain and swelling. While pain relief from a headache can be obtained with a single 200–400 mg dose of ibuprofen, a full anti-inflammatory effect for bursitis might require 3,200 mg/d of the same drug. NSAIDs fall in seven major classes: proprionic acid derivatives, indole derivatives, fenamates, pyrrolealkanoic acids, pyrazolone derivatives, oxicams and salicylic acids.

One possible reason that has emerged is the selectivity of different NSAIDs even within the same class for different forms of cyclooxygenase (COX) enzymes, which are involved in the production of prostaglandins. Researchers are seeking NSAID formulations that would inhibit COX-2, which is responsible for inflammation, while sparing COX-1, which produces the more protective prostaglandins. Those NSAIDs inhibiting COX-1 most strongly are also known to have greater ulcerogenic activity. NSAIDs that are relatively COX-2 selective, such as nabumetone and etodolac, may have a slightly lower risk of GI and renal adverse effects. Ringel M, Which NSAID for acute joint pain? Patient Care, Feb. 28, 1998. Chronic use of NSAIDs in older adults is also associated with an increased risk of renal dysfunction. Field T S, *J Am Geriatr Soc* 1999,47:507–511.

TABLE 1

| NSAID | Adult Daily Oral Dosage | Suggested Daily Topical Dosage |
| --- | --- | --- |
| Indomethacin | 200 mg | 50 mg |
| Sulindac | 400 mg | 100 mg |
| Tolmetin | 1,800 mg | 500 mg |
| Piroxicam | 20 mg | 5 mg |
| Diclofenac potassium | 200 mg | 50 mg |
| Diclofenac sodium | 200 mg | 50 mg |
| Fenoprofen | 3,200 mg | 800 mg |
| Flurbiprofen | 300 mg | 70 mg |
| Ibuprofen | 3,200 mg | 800 mg |
| Ketoprofen | 300 mg | 70 mg |
| Naproxen | 1,500 mg | 350 mg |
| Etodolac | 1,200 mg | 300 mg |
| Aspirin | 3,600 mg | 800 mg |
| Diflunisal | 1,500 mg | 350 mg |

Table 1 shows the recommended maximum daily oral dosage for some of the more popular NSAIDs and the suggested topical dosage for achieving the same anti-inflammatory benefits to the affected body part. The use of topical NSAIDs in humans and animals demonstrated a lower plasma concentration than with systemically administered drugs, but maintained the same anti-inflammatory effect. Vaile J H, Davis P, Topical NSAIDs for musculoskeletal conditions. A review of the literature. Drugs 1998 November;56(5):783–99. Topical diclofenac eye drops proved as effective as prednisone in controlling inflammation and discomfort after strabismus surgery. Apt L, Voo 1, Isenberg S J, A randomized clinical trial of the nonsteroidal eyedrop diclofenac after strabismus surgery. *Ophthalmology* 1998 August;105(8):1448–52. A study compared topical eltenac with oral diclofenac in osteoarthritis patients and found a similar symptomatic relief, but that the number of GI reactions were three times higher in the diclofenac group. Sandelin J, et al. Local NSAID gel (eltenac) in the treatment of osteoarthritis of the knee. A double blind study comparing eltenac with oral diclofenac and placebo gel. *Scand J Rheumatol* 1997;26(4):287–92.

The use of NSAIDs as analgesics and anti-inflammatory agents is well known in the art. Paradies, U.S. Pat. No. 5,604,206, discloses complexes of ibuprofen and amino sugars, but does not teach a transdermal preparation. Veronesi, U.S. Pat. No. 4,748,174, discloses a composition to improve GI absorption using meglomine or glucamine salt and an NSAID. Cavanaugh, Jr., U.S. Pat. No, 5,626,838, discloses a method to treat oral cancer with a topical composition of an NSAID. Adger et al, U.S. Pat. No. 5,811,558, discloses a process for preparing a salt of etodolac. Shunshine et al, U.S. Pat. Nos. 4,722,938, 4,780,463, and 4,923,898 all disclose a method and composition of an NSAID and a muscle relaxant. None of the above cited patents teach or suggest the use of the method and composition outlined in the present invention.

Topically applied NSAIDs are well known in the art. Inagi et al, U.S. Pat. No. 4,309,414, discloses an ointment comprising; indomethacin, glycol, alcohol, water, gelating agent and adjuvant. Kigasawa et al, U.S. Pat. No. 4,500,511, discloses a composition comprising clidanac, gelling agent, neutralizer, solubilizer, water and absorption promoter. Kamishita, U.S. Pat. No. 4,543,251, discloses a gel preparation comprising diclofenac, lower alkanol, water, glycol, carboxyvinyl polymer and aliphatic amine. Ogiso, U.S. Pat. No. 4,873,081, discloses a percutaneous absorption preparation of indomethacin, ethylene glycol, DMSO, gelatinizing agent and an absorption adjuvant. Kamiya et al, U.S. Pat. No. 4,948,588, discloses a preparation of aspirin and an absorption accelerator. Cooper et al, U.S. Pat. No. 4,954,487, discloses a topical composition of an NSAID, ethanol and penetration enhancing carrier. Betlach, II, U.S. Pat. No. 5,374,661, discloses a composition of diclofenac, thickening agent, alcohol, glycol, ether alcohol and fatty alcohol ester, water and neutralizing agent of ethoxydiglycol. None of the above cited patents teach or suggest the use of the method and composition outlined in the present invention.

Anti-inflammatory Agents

Inflammation is a fundamental pathologic process involving complex reactions that occur in the affected blood vessels and adjacent tissues in response to an injury or abnormal stimulation caused by a physical, chemical, or biologic agent. The acute inflammatory response begins after cellular injury due to microorganisms, physical agents (such as burns, radiation, and trauma), chemicals, necrotic tissue, and immunological reactions. Five classic signs are manifested in acute inflammation; redness, heat, pain and loss of function. These signs are induced by changes which take place in the microvasculature (arterioles, capillaries, and venules) and the interstitial areas (fluid-filled regions between cells and tissues). These include changes in vascular flow and caliber, changes in vascular permeability, and leucocyte exudation. The first change involves vasodilation of the vessels and increased blood flow. The second change involves increased permeability of the blood vessels with a movement of fluid and proteins out of the vessels creating edema of the tissues. The final change occurs as white blood cells infiltrate and accumulate in the surrounding tissue. The increased blood flow and permeability of the microvascular system at the inflamed body part facilitates treatment to the area by using a penetration enhancer to deliver the bio-affective agents.

The spread of the acute inflammatory response following injury to a small area of tissue suggests that chemical substances are released from injured tissues, spreading outwards into uninjured areas. These chemicals, called endogenous chemical mediators, cause vasodilation, emigration of neutrophils, chemotaxis and increased vascular permeability. Histamine is a chemical mediator in acute inflammation and causes vascular dilatation and vascular permeability. It is stored in mast cells, basophil and eosinophil leucocytes, and platelets. Histamine release is stimulated by complement components C3a and C5a and by lysosomal proteins released from neutrophils. Prostaglandins are a group of long-chain fatty acids derived from arachidonic acid. They increase vascular permeability, and platelet aggregation. Drugs such as aspirin and NSAIDs inhibit one of the enzymes involved in prostaglandin synthesis. Other chemical mediators include; leukotrienes, serotonin and lymphokines. Plasma contains four enzymatic cascade systems; complement, the kinins, the coagulation factors and the fibrinolytic system.

Chronic inflammations are characterized by a longstanding dull pain, and indurated swelling, and the presence of granulation tissue. The predominant cells seen in chronic inflammation are the mononuclear leukocytes, such as macrophages, lymphocytes, and plasma cells. A fibroblastic proliferation is seen more often than a fluid exudate. Some bio-affective agents with anti-inflammatory properties are the following:

Colchicine

Gout is a musculoskeletal disorder and common type of arthritis caused by an increased concentration of uric acid in joints, tendons, cartilage, and surrounding soft tissues. It is one of the oldest recorded diseases in man, and afflicts the joint at the base of the big toe but can also cause pain and swelling in other joints such as knees, ankles, hands and wrists. Gout is becoming more frequent since low dose aspirin and diuretics, such as hydrochlorothiazide, are commonly used in the adult population, which inhibit renal excretion of uric acid and lead to the symptoms of gout. The acute inflammation of gout is believed to be activated after neutrophils phagocytize urate crystals with the ensuing release of chemotactic and other substances capable of mediating inflammation. Chronic gout results in an invasion of the articular and periarticular tissues, with structural derangement and secondary osteoarthritis. The inflammatory response to urate crystals requires leukocytes to be present.

Colchicine, an alkaloid, is effective in treating gout and dermatoses such as psoriasis, and Sweet's syndrome. Sullivan T P, King LEJr, Boyd A S, Colchicine in dermatology *J Am Acad Dermatol* 1998 December;39(6):993–9. Colchicine inhibits neutrophil chemotaxis thus decreasing the inflammatory process. Ben-Chetrit E, Levy M, Does the lack of the P-glycoprotein efflux pump in neutrophils explain the efficacy of colchicine in familial Mediterranean fever and other inflammatory diseases?*Medica/Hypotheses* 1998 November;51(5):377–80. Colchicine is a microtubule depolymerizing agent and a competitive antagonist at the GABA (A) receptor. Bueno OF, Leidenheimer N.J., Colchicine inhibits GABA(A) receptors independently of microtubule depolymerization. *Neuropharmacology* 1998;37(3):383–90. Colchicine has no effect on uric acid levels; rather it stops the inflammatory process by inhibiting neutrophil migration into areas of inflammation, blocks the release of chemotactic factor, reduces mobility and adhesion of polymorphonuclear luekocytes, inhibits the production of leukotriene, and reduces the production of lactic acid. Eighty percent of patients are unable to tolerate an optimal dose of colchicine because of gastrointestinal side effects. Murray M, Pizzorno J, *Encyclopedia of Natural Medicine* $2^{nd}$ Ed. 1998 Prima Publishing, Rocklin, Calif. Early degenerative changes in cartilage and synovial tissues of the knee joint are manifested by pain and limitation of motion. In a controlled study, colchicine and diclophenac were irrigated into the knee joints and after two years an examination demonstrated less fissure formation and cartilage thinning and increased chondrocyte proliferation and replication. Doral M N, et al, The Role of Irrigation with Colchicine and Diclophenac Sodium in experimental gonarthrosis. First Biennial Congress of the International Society of Arthroscopy, Knee Surgery and Orthopaedic Sports Medicine, Buenos Aires, Argentina, May 11–16, 1997.

Colchicine causes microtubule depolymerization which leads to a loss of cytokine receptor expression and underlies the anti-inflammatory actions. Rao P, et al, Colchicine down-regulates LPS-induced granulocyte-macrophage colony-stimulating factor production in murine macrophages. *J Immunol* 1997 October 1;159(7):3531–9. Colchicine inhibits COX-2 derived prostenoids, including prostaglandin $E_2$ (PGE$_2$) and thromboxane $A_2$ (TXA$_2$). Pouliot M, et al, Monosodium urate microcrystals induce cyclooxygenase-2 in human monocytes. *Blood* 1998 March;91(5):1769–76. Colchicine blocks sodium channel transport and can block axonal nerve transport but spares C-fiber nociceptor function. Kingery W S et al, Colchicine treatment of the sciatic nerve reduces neurogenic extravasation, but does not affect nociceptive thresholds or collateral sprouting in neuropathic or normal rats *Pain* 1998 January;74(1):11–20.

The inventor is not aware of the use of colchicine as a topical composition to treat musculoskeletal disorders. Colchicine is given orally and the recommended dosage is 1 mg orally followed by 0.5–0.6 mg every two hours until symptoms cease, not to exceed a total dosage of 6–8 mg. The suggested topical dosage is 0.2–0.5 mg.

The use of colchicine as an anti-inflammatory agent is well known in the art. Eakins et al, U.S. Pat. No. 4,190,673, discloses an ophthalmic preparation of 0.1 to 2% colchicine to treat glaucoma. Brossi et al, U.S. Pat. No. 4,533,675, discloses a colchicine compound to treat gout. Sackler et al, U.S. Pat. No. 5,747,060, discloses a formulation for local anesthesia comprising an anesthetic, controlled release material and colchicine to prolong the duration of the local anesthesia. Bombardelli et al, U.S. Pat. Nos. 5,843,910, 5,880,160, discloses colchicine derivative compounds and method to treat tumors due to antiproliforative and cytotoxic effects. NSAIDs have also been cited for treating gout. Mullane, U.S. Pat. No. 4,663,345, discloses a method for lowering uric acid using etodolac. Gertner, U.S. Pat. No. 5,061,724, discloses a method for alleviating symptoms of gouty arthritis with a bandage of skin cream and indomethacin. None of the above cited patents teach or suggest the use of the method and composition outlined in the present invention.

Methyl-Sulfonyl-Methane

Methyl-sulfonyl-methane (MSM) or dimethyl sulfone is essentially DMSO with an extra oxygen molecule and lacks the lipid-solubility of DMSO, but can be coupled with another penetration enhancer. In the body, MSM gives up its sulfur to form methionine and cysteine for connective tissue. MSM is anti-inflammatory and analgesic and useful for muscle soreness and cramps, prevents cartilage degeneration and improves joint flexibility. The therapeutic dosage range for MSM is 2–10 grams orally per day. The recommended topical dosage range is 1–5 grams.

Numerous patents for MSM were filed by Herschler. U.S. Pat. Nos. 4,296,130, discloses a method for softening skin; 4,477,469 discloses a composition of MSM and carbamide to soften skin; 4,863,748 discloses a method for adding sulfur to the diet with MSM; 4,973,605 discloses a method for treating muscle cramps associated with arthritis with oral MSM; and 5,071,878 discloses a method for using MSM in a diet for sulfur and health reasons. None of the above cited patents teach or suggest the use of the method and composition outlined in the present invention.

S-Adenosyl-Methionine

S-adenosyl-methionine (SAMe) is the activated form of methionine. SAMe appears to counteract cytokines, protects cartilage, inhibits destructive free radicals, and may reverse the effects of homocysteine on cartilage and/or inhibit enzymes. SAMe increases the number of chondrocytes (cartilage cells) and proteoglycans (protein), and reverses the damaging effects of TNF. SAMe also has a natural antidepressant effect which is beneficial to those patients with musculoskeletal disorders.

The recommended oral dosage of SAMe is 1,200 to 1,600 mg per day. The suggested topical dosage of SAMe is 800 mg.

The use of SAMe is well known in the art. Fiecchi, U.S. Pat. No. 4,057,686, discloses the process for the preparation of salts of SAM. Stramentinoli et al, U.S. Pat. No. 4,454, 122, discloses a method to treat inflammation and pain using MTA. Zappia et al, U.S. Pat. No. 4,764,603, discloses a process for preparing stable salts of SAMe. Le Fur et al, U.S. Pat. No. 4,956,173, discloses a method and composition to treat the skin using SAM. Gennari, U.S. Pat, No. 5,128,249, discloses a process for producing SAMe. Kurobe et al, U.S. Pat. No. 5,166,328, discloses a SAMe derivative useful for treating stroke. Braganza et al, U.S. Pat. No. 5,196,402, discloses a method for treating pancreatitis using SAMe. Kawabata et al, U.S. Pat. No. 5,466,678, discloses a method of reducing nephrotoxicity of cisplatin therapy using SAMe. None of the above cited patents teach or suggest the use of the method and composition outlined in the present invention.

Zinc Compounds

Osteoporosis is characterized by progressive loss of bone architecture and mineralization leading too the loss of bone strength and an increased fracture rate. The skeleton is constantly being remodeled by a balance between osteoblasts, that lay down new bone, and osteoclasts, that break down or resorb bone.

Zinc plays a physiological role in the regulation of bone metabolism, by stimulating bone formation and mineralization and an inhibitory effect on bone resorption. Zinc activates aminoacyl-tRNA synthetase in osteoblastic cells, stimulates cellular protein systhesis, and inhibits osteoclast-like cell formation in marrow cells. Bone zinc content is decreased by development, with aging, skeletal unloading, and postmenopausal conditions. Zinc plays a role in the preservation of bone mass. Most zinc compounds, such as zinc sulfate, are useful for the prevention of osteoporosis, but a recent study confirmed that β-Alanyl-L-histidinato zinc (AHZ) has a potent effect on bone formation and calcification. Yamaguchi M, Role of Zinc in Bone Formation and Bone Resrporption, *J. of Trace F. Elements and Experimental Medicine* 1998;11:119–135.

Zinc compounds have anti-inflammatory and anti-infective properties. In a recent published article, Petrus E J et al., *Current Therapeutic Research*, 1998; 59/9: 595–607, the inventor served as chief investigator for a randomized, double-masked, placebo-controlled clinical study of the effectiveness of zinc acetate lozenges on common cold symptoms in allergy-tested subjects. Those subjects who used the zinc lozenges had both a shorter duration and severity of common cold symptoms. Those subjects who were positive for allergies, were more responsive to zinc by having a shorter duration of nasal symptoms. The study cited many references that reported the following benefits and effects of zinc compounds:

Zinc is an essential trace element in human biology that is known to be necessary for many biologic functions, such as growth, appetite, testicular maturation, skin integrity, mental activity, wound healing, and immune system maintenance. Approximately 300 enzymes are known to require zinc for their activities. Zinc deficiency in humans is widespread and is more prevalent in areas where the population subsists on cereal proteins. Clinical manifestations of zinc deficiency include: growth retardation, hypogonadism in males, neurosensory disorders, cell-mediated immunological dysfunctions, increased maternal morbidity, premature delivery, and adversely affects the proliferation, regulation and maturity of lymphocytes.

Zinc has been shown to be an essential element for the function of the immune system. Regarding the effect of zinc on allergies, it is known that mast cells have been implicated as mediators of Type I allergic reactions. Mast cell derived reactions result from the release of histamine, heparin, prostaglandins, SRS-A, and various vasoactive amines from granules on the surface of mast cells, possibly including kinins. One product of mast cell-induced inflammation is fever. The inhibitory effect of zinc on histamine release from mast cells are attributed to its action on the stabilization of the mast cell membrane. Zinc ions were found to stabilize cell plasma membranes and prevent induced histamine and vasoactive amine release from tissue mast cells. It has been observed that unsequestered zinc ions (4 to 20 millimolar) are released in inflammation from mast cell granules suggesting a common linkage with inflammation. Zinc is a competitive antagonist of the calcium-dependent IgE and f-met peptide mediated histamine release from human basophils and suggested that zinc compounds might be considered for the treatment of autoimmune disorders.

Zinc compounds are acknowledged as anti-inflammatory agents, as astringents and beneficial in wound healing, and have antimicrobial, antifungal and antiviral activity. Zinc is the active agent in formulations to treat diaper rash, decubitus ulcers, and abrasions. Zinc stabilizes the cell membranes and inhibits the formation of free radicals. Zinc also strengthens the integrity of blood vessel walls by reducing the membrane permeability and stopping bleeding. Unlike other metals, zinc is virtually nontoxic.

Canadian researchers reduced the progression of experimental osteoarthritis in dogs by inhibiting inducible nitric oxide synthase (NOS). Pelletier J P, et al. *Arthritis & Rheumatism* 1998;41:1275–1286. Pelletier reported that osteoarthritis cartilage produced an increased amount of nitric oxide (NO) due to an increased level of inducible nitric oxide synthase in cartilage chondrocytes. Nitric oxide plays an important role in autoimmunity and inflammation. Normal cartilage does not produce NO or express NOS unless stimulated with cytokines. In the joint, NO, produced in response to cytokine stimulation, exerts a number of catabolic effects on chondrocyte functions which would be expected to promote the degradation of articular cartilage. These effects of NO on chondrocytes include: inhibition of collagen and proteoglycan synthesis, activation of metalloproteinases, increased susceptibility to injury by other oxidants, inhibition of actin polymerization, and apoptosis. NSAIDs, such as aspirin, and to a lesser extent, sodium salicylate, and tetracycline inhibit the expression of NOS protein. Clancy R M, Amin A R, Abramson S B. *Arthritis & Rheumatism* 1998;41:1141–1151. Zinc is a very potent inhibitor of nitric oxide synthase (NOS). Cuajungco M P, Lees G J *Neurobiol Disease* 1997;4(3–4):137–69.

The dosage range of an oral zinc compound is 30 to 60 mg per day in divided doses. The suggested topical dosage range is 10 to 20 mg. Zinc compounds are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

The topical use of zinc compounds is well known in the art. Kelly, U.S. Pat. No. 5,624,675, discloses the use of a zinc salt, such zinc acetate or zinc propionate as a genital lubricant to reduce the risk of HIV infection. The above cited patent does not teach or suggest the use of the method and composition outlined in the present invention.

Aloe Vera Extract

Aloe vera has been well reported to have anti-inflammatory and analgesic properties, but its use in treating musculoskeletal disorders has only recently been described. One study treated patients with a diagnosis of fibromyalgia and/or chronic fatigue syndrome with aloe vera gel extract and found that there was a remarkable reduction in initial symptom severity and continued improvement during the course of the study. Dykman K D, Tone C, Ford C, Dykman R A, The effects of nutritional supplements on the symptoms of fibromyalgia and chronic fatigue syndrome. *Interg Physiol Behav Sci* 1998 January–March;33:61–71. Both topical and oral treatments with aloe vera were found to increase the synthesis of glycosaminoglycans and enhance would healing. Chithra P, Sajithlal G B, Chandrakasan G, Influence of Aloe vera on the glycosaminoglycans in the matrix of healing dermal wounds in rats. *J Ethnopharmacol* 1998 January;59(3). 179–86. Aloe vera also increased the biosynthesis of collagen. Chithra P, Sajithlal G B, Chandrakasan G, Influence of Aloe vera on collagen turnover in healing of dermal wounds in rats. *Indian J Exp Biol* 1998 Septemeber;36(9):896–901. Aloe vera mixed with a nitric oxide inhibitor (L-NAME) improved wound healing and prevented dermal ischemia by reversing the effects of thromboxane synthase. Effect of the combination of Aloe vera, nitroglycerin, and L-NAME on wound healing in the rat excisional model. *J. Altern Complement Med* 1997 Summer;3(2): 149–53.

The use of Aloe vera is well known in the art. Carpenter et al, U.S. Pat. No. 5,786,342, discloses a method of reducing symptoms associated with chronic respiratory diseases using acetylated mannan from aloe vera. Strickland et al, U.S. Pat. No. 5,824,659, discloses the use of a oligosaccharide from Aloe to inhibit the loss of skin immunocompetency from ultraviolet irradiation.

Chondroprotective Agents

Glucosamine from exogenous sources (food and supplements) may stop the progression of cartilage degradation and stimulate the production of new cartilage. Glucosamine absorbed by the gastrointestinal tract undergoes significant first-pass metabolism in the liver, with the resulting 26% bioavailibility. It is incorporated into plasma proteins as a result of hepatic metabolism, and concentrates in the articular cartilage. Clinical improvement of symptoms has been seen as early as one week after oral administration of glucosamine sulfate and has persisted for up to four weeks after discontinuation. Barclay T S, Tsourounis C, McCart G M. Glucosamine. *Annals of Pharmacotherapy* 1998;32:574–79. In a review of the studies on glucosamine sulfate, the reviewers concluded that the chondroprotective agent reduces joint pain and tenderness, provided pain relief and improved mobility in patients with osteoarthritis. Da Camara C C, Dowles G V, Glucosamine sulfate for osteoarthritis.

Ann Pharmacotherapy 1998 May;32(5):580–7.

Several commercial forms of glucosamine are available, including the sulfate, hydrochloride, and N-acetylglucosamine (NAG). Glucosamine hydrochloride has a higher concentration of glucosamine than the sulfate form. NAG is rapidly metabolized to make proteins and provides less glucosamine for cartilage repair. The composition of the invention could include one or a combination of the glucosamine forms. Patients have reported a more rapid response with higher oral dosages of glucosamine. The dosage range for glucosamine can vary from 500 mg to 3000 mg a day, in divided doses, depending on body weight and severity of symptoms. The suggested topical dosage ranges from 500 to 1,000 mg. Adverse effects reported from glucosamine are gastrointestinal, such as heartburn and epigastric pain. Because the half-life of glucosamine in the blood is relatively short, a topical composition of the compound could avoid the adverse effects and provide a more uniform blood level.

Chondroitin sulfates are the major GAG in cartilage, and has a synergistic effect with glucosamine. Dosage range of chondroitin sulfate is 250 mg to 1,000 mg per day in divided doses. A dosage range for a topical composition could be 100 to 300 mg.

The use of glucosamine and chondroitin as an oral composition are well known in the art. Henderson, U.S. Pat. No. 5,364,845, discloses a composition of glucosamine and chondroitin as an oral composition. Morrison, U.S. Pat No. 3,895,107, discloses the use of chondroitin sulfate, derived from shark cartilage as a treatment for inhibiting the development of atherosclerotic lesions. None of the above cited patents teach or suggest the use of the method or composition outlined in the present invention.

The composition may also include various additional agents and ingredients such as: preservatives, antioxidants, stabilizers, surfactants, emollients, anti-infective agents, adjuvants, thickening and gelling agents, anthocyanidins, proanthocyanidins, amino sugars, glycosaminoglycans, nitric oxide synthase inhibitors, zinc salts, manganese, magnesium, boron, and herbal derivatives.

The use of a topical, as opposed to an oral or parenteral form of the bio-affective agents offers four major advantages: they deliver a very high concentration of the bio-affective agents to the desired site; eliminate the possibility of gastrointestinal upset or ulcers; low potential for drug interactions and no skin irritation at the application site. This invention is further illustrated by the following examples which are to be regarded as illustrative only, and in no way limit the scope of the invention. The above-mentioned patents are hereby incorporated by reference.

EXAMPLE 1

| Topical Joint Analgesic Gel | |
|---|---|
| Ibuprofen | 5.0% |
| Carboxyvinyl polymers | 2.0% |
| Aloe vera gel | 1.0% |
| Propylene glycol | 20.0% |
| Glucosamine sulfate | 20.0% |
| Methyl-sulfonyl-methane | 10.0% |
| Ethanol | 10.0% |
| Triethanolamine | 1.0% |
| Zinc sulfate | 1.0% |
| Methyl paraben | 0.1% |
| Propyl paraben | 0.02% |
| Water | 29.9% |

The analgesic gel in Example 1 provides analgesia, anti-inflammatory and chondroprotective benefits when applied to painful joints.

EXAMPLE 2

| Topical Gel for Gout Symptoms | |
|---|---|
| Colchicine | 0.1% |
| Etodolac | 5.0% |
| Carboxyvinyl polymers | 2.0% |
| Aloe vera gel | 1.0% |
| Propylene glycol | 20.0% |
| S-adenosyl-methionine | 20.0% |
| Methyl-sulfonyl-methane | 10.0% |
| Ethanol | 10.0% |
| Triethanolamine | 1.0% |
| Zinc sulfate | 1.0% |
| Methyl paraben | 0.1% |
| Propyl paraben | 0.02% |
| Water | 29.8% |

The topical gel in Example 2 is applied to painful joints when the uric acid levels are elevated, a diagnosis of gout or pseudogout (calcium pyrophosphate deposition disease) had been made or gout is suspected due to the location and symptoms of the body part.

EXAMPLE 3

| Topical gel for osteoarthritis | |
|---|---|
| Diclofenac | 5.0% |
| Carboxyvinyl polymers | 2.0% |
| Aloe vera gel | 1.0% |
| Propylene glycol | 20.0% |
| Glucosamine sulfate | 20.0% |
| Methyl-sulfonyl-methane | 10.0% |
| Ethanol | 10.0% |
| Triethanolamine | 1.0% |

| Topical gel for osteoarthritis | |
| --- | --- |
| Zinc sulfate | 1.0% |
| Methyl salicylate | 1.0% |
| Methyl paraben | 0.1% |
| Propyl paraben | 0.02% |
| Water | 28.9% |

The topical gel of Example 3 provides analgesia, anti-inflammatory relief, protection from osteoporosis and chondroprotective advantages.

EXAMPLE 4

59 year old male with diagnosed osteoarthritis of the knees and gout of the first MTP joint (big toe) of the right foot was started on the gel in Example 3 to be applied to the knee area four times a day. Pain relief to the knees occurred after one day, swelling was reduced after 3 days and limitation of motion improved after one week. When a gout attack occurred, the gel in Example 2 was applied to the inflamed toe every two hours while the pain and swelling persisted. Relief was obtained after eight hours.

EXAMPLE 5

An 82 year old lady with diagnosed rheumatoid arthritis of the lower back was started on the gel in Example 1 to be applied over the lower back area four times a day. Relief from the pain in the lower back was obtained after eight hours and had improvement of her limitation of motion and mild sciatica.

Although illustrative embodiments of the invention have been shown and described, a wide range of modifications, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A method for the treatment of musculoskeletal disorders in mammals by the application of a topical composition comprising:
   a) an effective amount of penetration enhancers selected from a group consisting of: alcohols, polyols, sulfoxides, esters, ketones, amides, oleates, surfactants, alkanoic acids, lactam compounds, alkalols, dialkylamino acetates, and
   b) anti-inflammatory bio-affecting agents, 0.1% to 25% by weight of the total composition, selected from a group comprising: nonsteroidal anti-inflammatory agents, and colchicine, in a therapeutically acceptable gel vehicle,
so that, a means for the delivery of the bio-affecting agents through the protective outer layer of the skin, into the underlying tissues and into the vascular network of the targeted body part to reduce inflammation and provide relief.

2. The method according to claim 1, which further comprises additional agents selected from the group consisting of: analgesics, antioxidants, anti-infective agents, adjuvants, anthocyanidins, proanthocyanidins, muscle relaxants, nitric oxide synthase inhibitors, methyl-sulfonyl-methane, S-adenosyl-methionine, zinc compounds, aloe vera extract, amino sugars, glycosaminoglycans, manganese, magnesium, boron and herbal derivatives.

3. The method according to claim 1, wherein the topically applied composition comprises from 0.2 mg to 0.5 mg of colchicine as the ant-inflammatory bio-affecting agent.

4. The method according to claim 1, wherein the topically applied composition comprises from 0.2 mg to 0.5 mg of colchicine and a nonsteroidal anti-inflammatory agent.

5. The method according to claim 1, wherein the topically applied composition comprises from 0.2 mg to 0.5 mg of colchicine and 2.0% to 6.0% of etodolac as bio-affecting agents.

6. The method according to claim 1, wherein the topically applied composition comprises from 0.2 mg to 0.5 mg of colchicine and 3.0% to 6.0% of ibuprofen as bio-affecting agents.

7. The method according to claim 1, wherein the topically applied composition comprises from 0.2 mg to 0.5 mg of colchicine and 3.0% to 6.0% of diclofenac as bio-affecting agents.

8. A formulation for the treatment of musculoskeletal disorders in mammals by the application of a topical composition comprising:
   a) an effective amount of penetration enhancers selected from a group consisting of: alcohols, polyols, sulfoxides, esters, ketones, amides, oleates, surfactants, alkanoic acids, lactam compounds, alkalols, dialkylamino acetates, and
   b) anti-inflammatory bio-affecting agents, 0.1% to 25% by weight of the total composition, selected from a group comprising: nonsteroidal anti-inflammatory agents, and colchicine, in a therapeutically acceptable gel vehicle,
so that, a means for the delivery of the bio-affecting agents through the protective outer layer of the skin, into the underlying tissues and into the vascular network of the targeted body part to reduce inflammation and provide relief.

9. The formulation according to claim 8, which further comprises additional agents selected from the group consisting of analgesics, antioxidants, anti-infective agents, adjuvants, anthocyanidins, proanthocyanidins, muscle relaxants, nitric oxide synthase inhibitors, methyl-sulfonyl-methane, S-adenosyl-methionine, zinc compounds, aloe vera extract, manganese, magnesium, boron and herbal derivatives.

10. The formulation according to claim 8, wherein the topically applied composition comprises from 0.2 mg to 0.5 mg of colchicine as the bio-affecting agent.

11. The formulation according to claim 8, wherein the topically applied composition comprises from 0.2 mg to 0.5 mg of colchicine and a nonsteroidal anti-inflammatory agent.

12. The formulation according to claim 8, wherein the topically applied composition comprises from 0.2 mg to 0.5 mg of colchicine and 2.0% to 6.0% of etodolac as bio-affecting agents.

13. The formulation according to claim 8, wherein the topically applied composition comprises from 0.2 mg to 0.5 mg of colchicine and 3.0% to 6.0% of ibuprofen as bio-affecting agents.

14. The formulation according to claim 8, wherein the topically applied composition comprises from 0.2 mg to 0.5 mg of colchicine and 3.0% to 6.0% of diclofenac as bio-affecting agents.

15. The formulation according to claim 8, wherein the topically applied composition comprises: colchicine, etodolac, S-adenosyl-methionine, methyl-sulfonyl-methane, carboxyvinyl polymers, aloe vera gel, propylene glycol, ethanol, triethanolamine, zinc sulfate, methyl paraben, propyl paraben, and water.

* * * * *